United States Patent [19]

McClendon

[11] Patent Number: 4,998,984

[45] Date of Patent: Mar. 12, 1991

[54] PREMOISTENED PREPACKAGED DISPOSABLE DISINFECTANT WIPER

[76] Inventor: Evelyn McClendon, 233 Eastern Pkwy., Newark, N.J. 07108

[21] Appl. No.: 436,822

[22] Filed: Nov. 15, 1989

[51] Int. Cl.$^5$ .............................................. B65D 81/24
[52] U.S. Cl. ................................. 206/205; 206/440; 206/494; 206/361
[58] Field of Search ............... 206/205, 440, 494, 361

[56] References Cited

U.S. PATENT DOCUMENTS

| | | | |
|---|---|---|---|
| 3,657,760 | 4/1972 | Kudisch | 206/63.2 |
| 3,818,533 | 6/1974 | Scheuer | 15/104.93 |
| 3,881,210 | 5/1975 | Drach et al. | 15/104.93 |
| 4,045,364 | 8/1977 | Richter | 252/106 |
| 4,117,187 | 9/1978 | Adams et al. | 428/286 |
| 4,220,244 | 9/1980 | Elmorg | 206/210 |
| 4,362,781 | 12/1982 | Anderson | 428/291 |
| 4,575,891 | 3/1986 | Valente | 15/104.93 |
| 4,601,081 | 7/1986 | Sutton et al. | 15/104.94 |
| 4,627,936 | 12/1986 | Gould et al. | 252/558 |
| 4,762,124 | 8/1988 | Kerch et al. | 206/456 |
| 4,781,974 | 11/1988 | Bouchette et al. | 428/288 |

*Primary Examiner*—Joseph Man-Fu Moy
*Attorney, Agent, or Firm*—Arthur J. Plantamura

[57] ABSTRACT

A prepackaged single use disposable wiper pad or towelette that is saturated with a disinfecting liquid is prepared. The wiper pad is effective to disinfect inanimate surfaces such as telephone mouthpiece or toilet seat against a broad spectrum of infectious microorganisms including the HIV-1 or AIDS virus. The wiper pad is of a size which fits in a pocket or purse and makes it convenient to be carried safely by a person and poses no problem in disposing such as by flushing in a toilet.

20 Claims, 1 Drawing Sheet

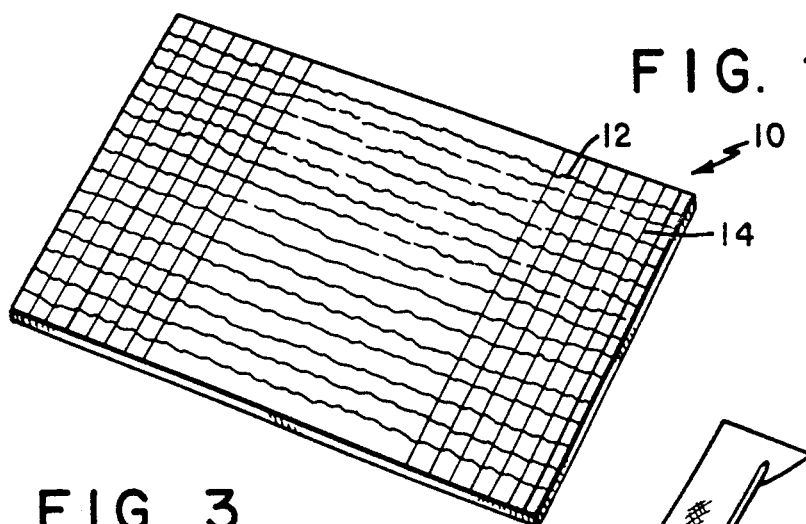
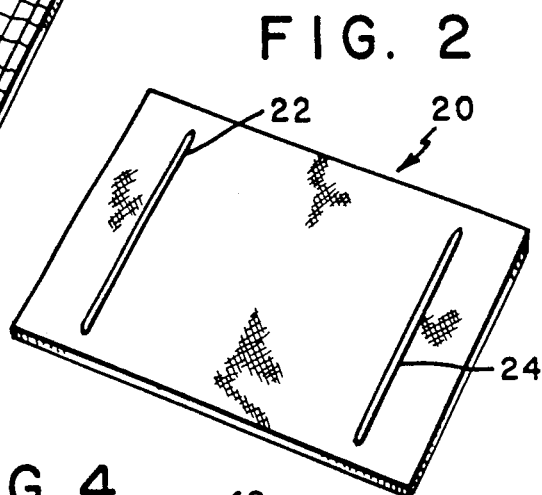
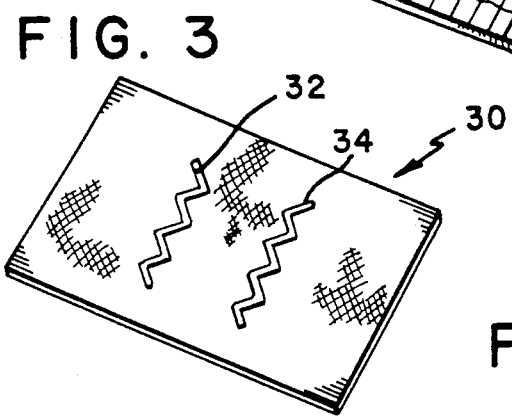
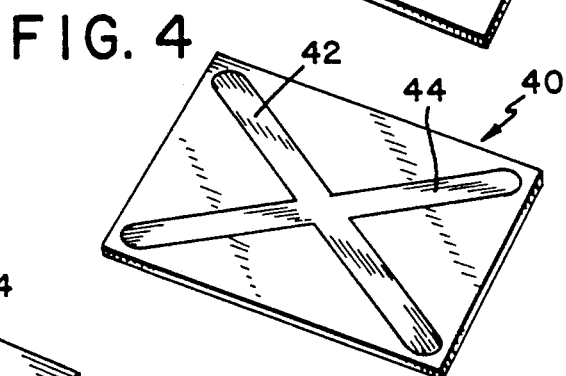
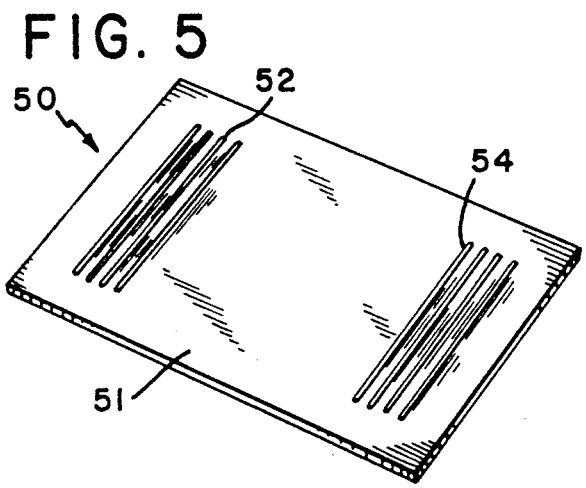
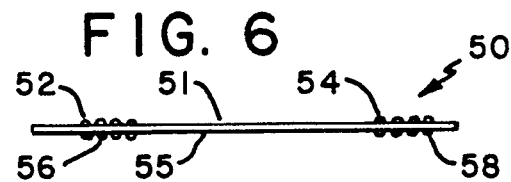
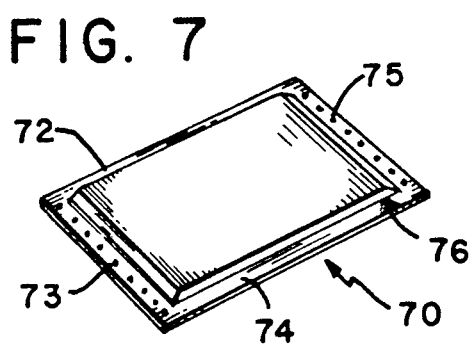
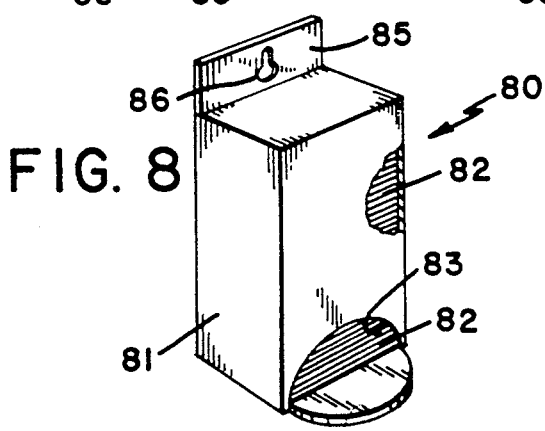

PREMOISTENED PREPACKAGED DISPOSABLE DISINFECTANT WIPER

This invention relates to a premoistened and prepackaged towelette for cleaning and disinfecting inanimate surfaces. In particular, the invention provides a single use premoistened prepackaged towelette or wiper that is effective in cleaning and decontaminating inanimate surfaces which may have been contaminated with a broad spectrum of harmful microorganisms, including the human imminodeficiency virus (HIV-1) or AIDS virus, salmonella, staphylococcus, streptococcus and others.

BACKGROUND OF THE INVENTION

Various prepackaged and premoistened disposable cleansing articles are known in the art for cleansing surfaces such as the disposable toilet seat wiping pad of U.S. Pat. Nos. 4,475,891 and 4,601,081, and the articles of U.S. Pat. Nos. 4,117,187 and 4,781,974 which describe premoistened wipers that are usable on parts of the human body and include antimicrobial active solutions. However, no prepackaged, conveniently available, already premoistened for instant use, wiper or towelette is known which is effective to decontaminate inanimate surfaces against a broad spectrum of harmful microorganisms, for example, bacteria or germs, and, more specifically, a single use wiper pad for removing soap scum and hard water salts which can harbor bacteria, and, generally, to clean hard non porous susrfaces such as tables, counters, walls, floors, carts, and other food processing, preparation and servicing facilities, in hospitals, veteranary clinics, animal research facilities and in other indoor areas where anti-bacterial control measures are essential or highly desirable including means to guard against the more resistant viral contaminants such as the HIV-1 or AIDS virus and toxic microorganisms such as salmonella.

Accordingly, a need exists for a convenient, readily available, i.e., accessible, sterile prepackaged premoistened disposable towelette which is effective to disinfect or decontaminate surfaces which may have become contaminated by contact with a variety of microorganisms from infected persons, articles or materials, such as those contaminated with the HIV-1 virus.

SUMMARY OF THE INVENTION

It is, accordingly, an object of the invention to provide a packaged premoistened disposable single use wiper pad that is useful in decontaminating inanimate surfaces.

It is a further and more particular object of the invention to provide a readily available premoistened, prepackaged disposable disinfectant wiper pad that is effective to decontaminate, or rid, an inanimate surfaces of a broad range of microorganisms, including hazardous and often contageous contaminants, such as those known as the HIV-1 and AIDS viruses.

It is a further and more specific object of the invention to provide a prepackaged disposable single use wiper which is saturated with a liquid disinfectant and conveniently available for use on inanimate surfaces. The wiper pad being premoistened with a liquid disinfectant that is an effective cleanser and decontaminant against a wide range of microorganisms that are harmful to humans, said disinfectant being an effective germicide, fungicide, tuberculocide and virucide, as well as functioning to control or eliminate undesirable odors.

It is a further object of the invention to provide an economical versatile and readily available premoistened prepackaged disposable wiping article for cleansing and decontaminating inanimate surfaces, that is easily manufactured such as from a web of material, which may be such as a non woven fabric of suitable composition, e.g. cotton or other cellulose material, rayon, polyester, jute, etc or mixtures thereof. The wiper pad or towelette article of suitable size, e.g., of the order of about 4 to about 64 square inches, and thickness may be premoistened and sealed in a suitable moisture, and preferably light impermeable barrier packet or such as, for example, the envelope package described in U.S. Pat. No. 4,627,936. In the packaging scheme of that patent, a nozzle is inserted into an open end of the envelope, and a measured quantity of the wiper pad saturating disinfecting solution, such as that of the kind to be described hereinbelow, is injected into the envelope and the envelope is sealed. The premoistened wiper pad, sealed within the envelope, then becomes substantially uniformly saturated with the disinfecting solution by capillary action and is readily available, suitably wetted for instant use, simply by tearing open the enclosing air tight liquid impermeable envelope. The sealed packets of the invention premoistened with disinfectant may be prepackaged in suitable quantities in a dispensing container, i.e., the con be devised to be conveniently mounted, such as on a wall, in the area where wiper pads are likely to be needed, such as in a clinic.

Other objects and advantages of the invention will become apparent from the following detailed description of the invention when considered in conjunction with the accompanying drawing.

BRIEF DESCRIPTION OF THE DRAWING

FIG. 1 illustrates one embodiment of the invention comprising one form of the premoistened wiper.

FIG. 2 illustrates an alternative form of the premoistened wiper pad of the invention provided with a pair of ridges that enhance the grip of the wiper pad when in use.

FIG. 3 illustrates another embodiment of the invention in which the pad is provided with a different form of finger gripping means which is more centrally located on the wiper pad.

FIG. 4 illustrates still a further embodiment in which the premoistened wiper pad is provised with an integrally incorporated reiinforcing means whereby the pad may better resist disintegration.

FIG. 5 illustrates a further embodiment in which the wiper pad of the invention is provided with a plurality of integrally incorporated upper gripping ridges and underside ridges, the latter enhancing the scouring capability of the premoistened pad when the pad is functioning to wipe a contaminated surface that may contain some encrustation.

FIG. 6 is an vertical end view of the wiper pad of FIG. 5.

FIG. 7 is a perspective view of a typical sealed packet or container encapsulating the premoistened wiper pad of the invention.

FIG. 8 is a perspective view of a typical dispenser unit for housing a supply of the individual wiper packets; the dispenser optionally functioning also as a shipping container package and devised for conveniently being suspending on a wall in the area of potential use to dispense, individually, the sealed wiper packets.

DETAILED DESCRIPTION OF THE INVENTION

The invention provides a novel readily available premoistened disinfecting, single use, wiping pad that can be used to decontaminate inanimate surfaces that may have been exposed to organic soil, such as blood serum, viruses, salmonella and other infectuous or harmful microorganisms. The availability of the premoistened prepackaged wiper pad obviates the need to first require the preparation and/or premixing or transporting and dispensing of a disinfecting solution onto a wiper article.

The relatively small tear open package of the premoistened disposable inanimate surface decomtaminating wiper pad of the invention affords a needed convenience for the many instances when it is not convenient, and sometimes not practical, to have a disinfectant solution available. This need is becoming more pronounced because of the increasingly serious need to disinfect surfaces to inhibit the spread of disease by viruses, the most notorious of which is the HIV-1 or AIDS virus, as well as other microorganisms. Many of these microorganisms are resistant to elimination by conventional cleaning means, i.e., ordinary soaps or detergents, and it is important that such contaminants be cleansed from many surfaces, especially those that are used as work surfaces, e.g., in the preparation of food or in medical treatment, to avoid the spread of germs. Included among the various contaminants that the wiper pad of the invention may effectively remove from surfaces are: soap scum and hard water salts that tend to harbor bacteria; organic matter such as blood, spilled food stuffs, dirt, dust, and the like. The premoistened wiper pad of the invention is particularly effective for use on washable, substantially non porous sufaces, such as counters, tables, walls, floors, carts, utensils, tools and other equipment used in food processing, preparation and servicing facilities, human and veteranery clinics, animal research facilities, toilets, and work areas, and other indoor areas where anti-bacterial control measures are necessary or desirable. The premoistened wiper pad of the invention makes immediately available a means to immediately wipe clean, disinfect and deodorize surfaces. Surfaces against which the wiper pad of the invention is particularly effective are such as stainless or galvanized steel, chrome, procelain, plastic glass, tile, washable painted or varnished surfaces and concrete, as well as the more resilient surfaces, such as vinyl, asphalt, linoleum, rubber, terrazzo, and other types of floors and counters.

The premoistened prepackaged wiper pad of the invention may function as:
(a) a germicide, to neutralize microorganisms such as S. Aureus, S. chloeraesuis and Ps. aeruginosa;
(b) a broad spectrum decontaminant, against various microorganisms such as salmonoella typhi, staphylcoccus aureus, streptcoccus epidermidis, and the like, as listed on the the label of the o-phenylphenol/p-tertiary amylphenol germicidal detergent available under the brand name LpHse from the Calgon Vestal Laboratories division of Calgon Corporation, a subsidiary of Merck & Co., Inc., St. Louis, Mo.
(c) a fungicide, effective against microorganisms such as T. mentagrophytes.
(d) a tubercolocidal, effective against such as Mycobacterium tuberculosis.
(e) a virucidal, effective against such as Herpes simplex Type 2; and
(f) an odor control device for killing odor-causing bacteria while simultaneously chemically neutralizing their odors.

The single use, disposable wiper pad of the invention, premoistened with an effective microorganism decontaminating solution, and prepackaged in a flexible air tight container, to be conveniently carried in a purse or pocket supplies an effective mechanism to rid lavatory, clinics, services areas, and other environments of the foregoing and other contaminant hazards.

The substrate or cloth portion of the wiping pad of the invention may comprise any of various known fabrics that are suitable for wiping a surface. Such substrate materials should be capable of absorbing and retaining a substantial quantity of the disinfecting liquid. Such substrates may comprise various compositions such as, paper, cloth of natural or synthetic fiber, or a sponge-like synthetic composition, such as plyurethane foam. Also, the composition of the pad should be such that it resists disintegration in use for a time to effect suitable wiping of the surface to be cleaned before the pad is discarded. Preferably the wiper pad substrate, to render it more desirable from an environmental standpoint, may be biodegradable, i.e., comprises a material whose decomposition is accelerated upon exposure to air.

The wiper of the invention may be of any convenient size and thickness suitable for the purpose and may vary, for example, from about two to about 200 square inches when unfolded, although, for convenience and for most practical "portable" purposes, a wiper pad having a surface area of from about 4 square inches to about 100 square inches is preferred. In particular, the size of the wiper pad for many applications, when it is desired to have it available for immediate use as a premoistened disinfectant wiper pad for an inanimate surface should comprise a square of about seven inches on a side or a surface area or about 50 square inches. However, for many applications, such as for wiping a telephone mouthpiece or an ear insert, such as the kind which accompanies a tour guide cassette, for example, a smaller size wiper pad such as about 9 square inches is adequate and is carried more conveniently in a purse. For some uses, it may be important that the premoistened wiper, in its unfolded state (assuming the pad is folded when packaged), be of a size sufficient to cover the hand and separate the had from the surface being wiped. For industrial use, on the other hand, an unfolded wiper having a size preferable of at least about 8 to 12 inches on a side, i.e., having an area of from about 60 to about 150 square inches is more suitable. The thickness of the wiper pad fabric should be sufficient to absorb and retain adequate moisture when saturated to at least dampened the contaminated surface to be disinfected. This may depend on the composition of the pad. For example, a pad of a given size and thickness of 100 percent cotton will absorb a greater volume of solution than a pad comprising a blend of say 75 percent cotton and 25 percent synthethic fiber, e.g., polyester or nylon, yet the latter fabric will have greater tear or decomposition resistance. A wiper pad having a thickness of from about 0.01 inch to about 0.15 inch, and preferably a thickness of from about 0.02 to about 0.1 inch is sufficient for most applications and moisture retention. The relatively small size of the wiper pad is desirable to permit ready disposition of the used pad such as by flushing in a toilet without any significant tendency to cause a blockage, due to the bulk of the wiper.

The substrate material which is moistened and prepackage with the decontaminating solution, as has been mentioned, may comprise any of known suitable fabrics, both woven and non-woven webs. Suitable web materials for the wiper pad may comprise conventional cotton wipers, such as those available in various sizes as "sterile pads" in a pharmacy or in stores which have a patent medicine and toiletries section. Typical of such pads are those available in 2×3, 2×3 and 4×4 inch size under the brand same Steri-Pad from Johnson & Johnson, Consumer Products, new Brunswick, N.J. Non woven fabric material which may be employed as the pad may be such as the described in U.S. Pat. No. 4,117,187 comprised of wood pulp fiber bonded together with a suitable adhesive for the fiber and may include, also, a wet strength enhancer for the fabric substrate. It will be readily understood by those skilled in the art that the adhesive binding the fiber of the pad fabric and lending integrity to the wiper pad, as well as any wet strength enhancing additive, must be compatible and be sufficiently resistant to the decontaminating solution to maintain the intended purpose at least until the desired wiping function has been completed. Thereafter, decomposition of the substrate fabric material is prefereably accelaerated upon exposure of air.

When the wiper pad of the invention is formed from woven fabric substrates, and which amy be relatively more resistant to decomposition or disintegration, e.g., cotton, jute, or synthetic fibers, such as rayon, polyester, acrylonitrile fiber, nylon, and blends of such fibers, it is preferred that the size of the wiper pad be not larger than about six inches square in order to minimize any difficulty attendant with the disposal of the pad.

The cleansing and decontaminating effectiveness and/or sterilizing activity of the wiper pad of the invention is provided by any of various known compositions that are in liquid form, or can be converted into liquid form that will impregnate and saturate the wiper fabric substrate, i.e., a solution or slurry form, and that are generally toxic to disease carrying microorganisms. Such decontaminating pad moistening solutions or slurries are used only in amounts that are suitable to provide the desired disinfecting effect when used in wiping and such that the amount in the premoistened wiper pad would not present a significant hazard to humans in a normal use of the pad on an inanimate surface.

Suitable disinfecting compositions of this kind include sodium hypochlorite, available commercially as household bleach in solutions of 5.25%; alky, aryl or arylalkylchlorides, such as dimethylbenzyl ammonium chloride, available commercially in concentrations of 2.7% under the brand name Lysol; and the mixed solutions of dimethylethyl benzyl ammonium chloride and dimethyl benzyl ammonium chloride in a concentration of about 1.58 under the brand name King Pine; and various other known disinfectants such as those containing diethylene and/or methylene glycol.

Particularly, effective compositions used in the saturation of the wiper pad of the invention for the decontamination of inanimate surfaces, and which are known to be effective, are various known phenol and xylenol containing compositions, i.e., those containing one or more of the various phenols and xylenols. Included are a wide variety of phenols having suitable volatility, i.e., boiling points, and molecular weight, such as 2-amino-3-nitrophenol; 2--amino-4-nitrophenol, 2-amino-5-nitrophenol; 2-amino-6-nitrophenol, 3-amino-5-nitrophenol; 4-amino-2-nitrophenol, 4-amino-3-nitrophenol; 5-amino-2-nitrophenol o-, m- or p-amoxyphenol; p-amylphenol; p-tertiaryamylphenol; o-, m- or p-anilinophenol; o-, m- or p-benzylphenol; o-, m- or p-bromophenol; o-, m- or p-butoxyphenol; o-, m- or p-butyl phenol; p-sec-butylphenol; p-tert.-butylphenol; 2-chloro-4-nitrophenol; 2--chloro-5-nitrophenol; 4-chloro-5-nitrophenol; 5-chloro-2-nitrophenol; p-cyclohexylphenol; 2,3-dichlorophenol; 2,4-dichlorophenol; 2,5-dichlorophenol; 2,6-dichlorphenol; 3,4-dichlorophenol; 3,5-dichlorophenol; m-diethylaminophenol; 2,3-dimethoxyphenol; 2,6-dimethoxyphenol; 2,3-dinitrophenol; 2,4-dinitrophenol; 2,6-dinitrophenol; 3,4-dinitrophenol; 3,5-dinitrophenol; p-isoamylphenol; o-, m- or p-phenylphenol; o-, m- or p-propoxyphenol; 2,3,5-trichlorophenol; 2,4,6-trichlorophenol; xylenols such as 2,4-xylenol; 2,6-xylenol; 3,4-xylenol; and the like.

Such active compounds are used in relatively dilute solutions, i.e., containing a small but effective quantity of the phenol compound. Concentrations of the order of about 0.01 percent to about 0.8 percent of the phenol compound in solution and preferably a concentration of from about 0.02 to about 0.5 percent provides suitable results.

Among the more effective phenol type compositions are the phenylphenols and amylphenols, and mixtures, such as the substantially equal mixture of o-phenyl phenol and p-teriary amylphenol. A product of this kind, i.e., containing a mixture of o-phenyl phenol and p-teriary amylphenol, is marketed under the brand name LpHse from the Calgon Vestal Laboratory division of Merck & Co., Inc., St. Louis, Mo. as a 14.7% concentration. In use, a composition of this kind is diluted in water in a ratio of 1 ounce to 2 gallons of water to produce the surface wiping solution.

Another commercially available composition of this kind is the o-phenylphenol (2.8%) o-benzyl-p-chlorophenol ethyl alcohol (1.8%), xylenol (1.5%) isopropyl alcohol (0.9%), tetrasodium ethylenediamine tetraacetate (0.7%) annnd soap (16.5%) also available commercially as a disinfectantunder the brand name Lysol.

In preparing the premoistened prepackaged wiper pad of the invention, any of various suitable methods may be used. For example, the web may be saturated with the liquid disinfectant and then encapsulated or otherwise sealed in an air tight liquid impermeable package, preferably a flexible envelope type packet of a kind that is known for sealing in moisture laden inserts and optionally also opaque to light. Alternatively, the wiper pad of the desired dimension may first be enclosed in a packet or package in a dry condition and thereafter a measured amount of the active solution injected into an aperture in an otherwise sealed package and the aperture sealed; the solution thereafter being absorbed into and saturating the pad. This type of procedure is described, for example, in U.S. Pat. No. 4,627,936.

When the wiper pad is first premoistened before being packaged in the impermeable packet, the pad precursor in the form of a web having the desired width is passed through a bath of the disinfecting liquid with retention time sufficient to saturate the web, the web segmented or cut to the desired length, and the segments then sealed in the package.

The wiper pad of the invention is ideally suited to be carried by a person in a packet or purse and, because it is premoistened, it is available immediately for use for wiping in a one-step cleaning operation; when so used in wiping an inanimate surface, the premoistened wiper pad functions to effectively disinfect and deoderize the surface. Typical surfaces which may be effectively cleaned and disinfected, for example, include those, as mentioned heretofore, that are relatively non porous, such as, stainless steel, galvanized steel, chrome, porcelain, plastic, glass, tile, concrete, vinyl, asphalt, linoleum, rubber, and the like, The premoistened wiper pad is effective to cleanse, disinfect, deodorize, remove soil such as infectious deposits, including blood and other body fluids, soap scum, hard water salts, dirt and dust, and the like, which may harbor bacteria. Articles which it may be desirable to decontaminate include, among others, telephone mouth and ear pieces, toilet seats, tools and equipment, counter tops, walls, floors, utensils in cafeterias and other eating areas, in clinics, doctors and dentists offices and other treating spaces and service facilities, wherever anti-bacterial control measures are necessary or desirable.

When it is desirable to use the wiper pad of the invention, it is only necessary to tear open the the sealed envelope or other easily openable package containing the premoistened wiper pad and fully wiping the surface, which it is desired to disinfect, sufficiently to assure that the surface is satisfactorily treated, i.e., coated with the wiper pad disinfectant liquid or solution with which the pad is saturated.

The premoistened prepackage wiper of the invention is devised to be inexpensive so that it is economically practical to be a used freely as a single use disposable article cleansing pad. Immediately after its use, the wiper pad is easily discardable such as by flushing in a toilet. Also, because of the relatively small size of the single use wiper pad, e.g., a rectangle preferably of a size less than about ten-inches on a side, the premoisted prepackage wiper pad can easily be stored and carried, without being significant "excess baggage," in a pocket, purse or brief case, for immediate availability when needed. When used in a clinic, laboratory or other service area, such as when the wiper is dispensed from a wall-mounted container, the wiper size may be considerably larger such as from about 144 to about 400 square inches or more.

Referring to the drawing, as shown in FIG. 1, a pad 10 is shown of suitable thickness, of the order of about 0.05 inch to about 0.15 inch, and formed of a relatively loose weave having warp and woof threads, shown as 12, and 14, respectively, of absorbent composition such as cotton. The wiper pad is capable of absorbing and retaining in a saturated state, without dripping, a significant quantity of the liquid disinfectant. The pad may have any suitable shape such as rectangular, round, oval, and the like and may comprise a single layer thickness or multiple layers.

In the embodiment illustrated in FIG. 2, the pad 20 is provided with integrally formed, or applied ridges or strips 22 and 24 which function to minimize slippage from the hand during the wiping action.

In the embodiment of FIG. 3, the wiper 30 is provided with another form of gripping means, comprising at least one, more centally located, element two of which, 32 and 34, are shown in the form of a zig-zag pattern. In a relatively larger pad, such as one of the order of at least about 6 inches on a side, a more centrally located element which may be a single applique (although two are shown in FIG. 3 as 32 and 34) usually suffices.

The wiper pad 40 of FIG. 4 is provided with a reinforcing element in the form of cross strips, 42 and 44, which in addition to lending added strength in retaining the integrity of the pad, especially a pad formed of non woven fabric, functions to inhibit premature disintegration of the pad in the wiping action and also as a gripping means to aid in a firmer hold with the fingers during the wiping action.

FIG. 5, and the edge view of this embodiment shown in FIG. 6, comprises an additional embodiment in which ridges are provided on both faces of the pad 50, with the ridges 52 and 54, on surface 51 functioning as gripping means while the ridges 56 and 58 on the opposite side 55 functioning to provide enhanced abrading action on the surface to be treated during the wiping action.

FIG. 7 illustrates one form of an encapsulating envelope 70 having a generally rectangular shape and formed of an air and liquid impermeable and, preferably also of an air and light impermeable construction and which is sealed on all sides 72, 73, 74 and 75 and, optionally provided with a notch 76 to facilitate the tearing open of the package at the time of use.

FIG. 8 illustrates a dispensing package 80 which may function as a shipping package and as a dispender for the premoistened wiper sealed . individual packets shown as 82 stacked vertically in the container 81. The package or container 81 may conveniently have a width and depth of about 4 inches and a height of about 8 or more inches so as to hold a convenient number, e.g., of the order of about 50 to about 100 sealed wiper packets. The container 81 may comprise a perforated opening 83 at the bottom front of the container 81, which when opened, provides dispensinsing extension 84 at the bottom to hold a next packet in sequence after a prior packet has been withdrawn. An upper folded-over extendable flap 85 may also be provided at the top for convenience in attaching, i.e., suspending, the dispensing container 80 at a suitable location, such as on a convenient wall in a clinic, for example. A keyhole shaped opening 86 is shown in the flap 85 to facilitate attachment of the suspended package 80 on a screw or nail secured on a wall or other supporting.

The following examples are provided as illustrative of the invention, but should not be construed as limiting of the invention to the specific details thereof.

EXAMPLES 1-3

Preparation of the Disinfectant

Preparation A: A liquid composition comprising a solution comprising a 2.7% alkyl (50% $C_{14}$, 40% $C_{12}$ and 10% $C_{16}$) dimethyl benzyl ammonium chlorides solution available as Lysol Brand Cleaner was used in the commercially obtained concentration of 2.7% to saturate wiper pads.

Preparation B: A solution of sodium hypochlorite, household bleach, purchased commercially under the brand name, Clorox, and having a concentration of 5.25 sodium hypochlorite was diluted by adding 0.75 cup of the bleach in a gallon of water (to a concentration of about 0.35%) to comprise the wiper pad saturating disinfectant liquid.

Preparation C: A liquid composition comprising a solution of 7.3% o-phenylphenol and 7.4% p-tertiary amylphenol in a concentration of 14.7% available commercially as a one-step germicidal detergent under the registered trademark LpHse from Calgon Vestal Laboratories Division of Calgon Corporation, a Subsidiary of Merck & C., Inc., St. Louis, Mo. This composition was diluted to a concentration of 0.06 percent by weight of the phenol blend in water. This diluted solution was used to thoroughly saturate the wiper pads.

Impregnation/Saturation of the Wiper Pads

Cotton wiper pads, 2 inches by 2 inches in size, were impregnated/saturated, respectively, in each of the Preparation A, B and C, prepared as above, and were then individually wrapped and sealed in a moisture and light-impermeable package and allowed to stand for six weeks.

Test of the Disinfectant Capacity

To test the disinfecting effectiveness, three glass slides were prepared and the surface of the slides contaminated with a 5% blood serum containing the HIV virus in a hospital laboratory.

The sealed packages containing the wiper pads premoistened with the above-described Preparations A, B and C were opened and each used to wipe, respectively, in a single stroke, the contaminated surface of the prepared glass slides. The surfaces of the glass slides were then examined under a microscope. The examination showed that the wiping action disinfected the HIV virus that had contaminated each of the slides. The stability of the disinfectant power of the premoistened wiper pad that has been sealed in a moisture and light barrier package is projected to retain its effectiveness for at least 24 months under normal storage conditions.

Another effective commercially available liquid composition suitable diluted or in full strength is that available under the the brand name Lysol Disinfectant; this composition comprises 2.8% o-phenylphenol; 2.7% o-benzyl-p-chlorophenol; 1.8% ethyl alcohol; 1.5% xylenol; 0.9% isopropylalcohol; 0.7% tetrasodium tetraacetate; and 16.5% soap in a concentration of 26.9%.

It is thus seen that the invention provides a novel and convenient single use, disposable wiper pad which is readily available as a premoistened wiper pad that is saturated, and maintained moist until used, with an effective microorganism disinfecting liquid. The saturated pad is packaged in a flexible air tight container, permitting it to be conveniently portable so as to accompany the user, such as by being carried in a purse or pocket.

While the invention has been described to particularly disclose the presently most preferred embodiments of the invention, it will be recognized that the invention may take various other forms that are within the scope of the invention as disclosed. Accordingly, it will be understood that the invention should not be limited except as may be required by the scope of the claims which follow.

What is claimed is:

1. An article of manufacturing comprising a disposable wiper pad which is impregnated, and is retained premoistened, with a liquid disinfectant composition that is effective to cleanse by wiping from an inanimate substantially nonporous surface, a broad spectrum of infectuous microorganisms including that identified as the human immunodeficiency virus, said composition comprising from about 0.01 percent to about 1.0 percent based on the weight of the liquid composition of a disinfectant selected from the group consisting of phenol, xylenol and sodium hypochlorite, said premoistened wiper pad being prepackaged in a container which is substantially liquid impermeable.

2. The article of claim 1 wherein the container is substantially impermeable to light.

3. The article of claim 1 wherein the disinfectant is a phenol.

4. The article of claim 3 wherein the disinfectant is a xylenol.

5. The article of claim 1 wherein the disinfectant is sodium hypochlorite.

6. The article of claim 1 wherein the disinfectant is a blend of a phenol and a xylenol.

7. The article of claim 1 wherein the premoistening phenol solution is a non-alkaline germicidal detergent.

8. The articl of claim 3 wherein the disinfectant comprises o-phenylphenol.

9. The article of claim 3 wherein the disinfectant comprises p-tertiary amylphenol.

10. The article of claim 3 wherein the disinfectant comprises a blend of o-phenylphenol and p-tertiary amylphenol.

11. The article of claim 1 wherein the pad substrate comprises a non-woven fabric.

12. The article of claim 1 wherein the wiper pad has thickness not greater than 3/16 inch and an area of at least about four square inches.

13. The article of claim 1 wherein the wiper pad substrate is composed of a composition is biodegradable when exposed to air.

14. A method for preparing a premoistened single use disposable wiper pad which is impregnated with a liquid disinfectant and which is an effective disinfectant against a broad spectrum of infectious microorganisms including the HIV virus which comprises saturating and thereby substantially impregnating an absorbent fabric substrate with from about 0.01 percent to about 1.0 percent based on the weight of the solution of a disinfectant liquid selected from the group consisting of phenol, xylenol and sodium hypochlorite, and enclosing
said premoistened wiper pad in a container which is substantially liquid impermeable.

15. The method of claim 14 wherein the container comprises a tear-open packet.

16. The method of claim 14 wherein the fabric substrate is impregnated with a phenol.

17. The method of claim 14 wherein the fabric substrate is impregnated with a bled of o-phenylphenol and p-tertiary amylphenol.

18. The method of claim 14 wherein the fabric substrate is impregnated with xylenol liquid.

19. The method of claim 14 wherein the fabric substrate is impregnated with sodium hypochlorite.

20. The article of claim 1 wherein the face of the pad includes means that afford enhance abrading action.

* * * * *